US00PP35484P2

(12) United States Plant Patent
Tashiro

(10) Patent No.: US PP35,484 P2
(45) Date of Patent: Nov. 14, 2023

(54) ***SUTERA* PLANT NAMED 'BALMECOPLUM'**

(50) Latin Name: *Sutera cordata*
Varietal Denomination: Balmecoplum

(71) Applicant: Ball Horticultural Company, West Chicago, IL (US)

(72) Inventor: Rebecca M. Tashiro, Nipomo, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/123,831

(22) Filed: Mar. 20, 2023

(51) Int. Cl.
*A01H 5/02* (2018.01)
*A01H 6/00* (2018.01)

(52) U.S. Cl.
USPC ..... Plt./485

(58) Field of Classification Search
USPC ..... Plt./485
See application file for complete search history.

*Primary Examiner* — Susan McCormick Ewoldt
(74) *Attorney, Agent, or Firm* — Audrey Charles

(57) ABSTRACT

A new and distinct cultivar of *Sutera* plant named 'Balmecoplum', characterized by its dark purple-colored flowers, dark green-colored foliage, low growth vigor, and a mounded-trailing growth habit, is disclosed.

1 Drawing Sheet

Latin name of genus and species of plant claimed: *Sutera cordata*.
Variety denomination: 'Balmecoplum'.

BACKGROUND OF THE INVENTION

The present invention relates to a new and distinct cultivar of *Sutera* plant botanically known as *Sutera cordata* and hereinafter referred to by the cultivar name 'Balmecoplum'.

The new cultivar originated in a controlled breeding program in Arroyo Grande, California during April 2017. The objective of the breeding program was the development of *Sutera* cultivars that have large-sized flowers and a mounded-trailing growth habit suitable for hanging basket, and container use.

The new *Sutera* cultivar is the result of cross-pollination. The female (seed) parent of the new cultivar is the proprietary *Sutera cordata* breeding selection coded SUT-1039-004, not patented, characterized by its medium pink-colored flowers, dark green-colored foliage, low growth vigor, and mounded-trailing growth habit. The male (pollen) parent of the new cultivar is the proprietary *Sutera cordata* breeding selection coded SUT-0906-001, not patented, characterized by its medium violet-blue colored flowers, dark green-colored foliage, low growth vigor, and mounded-trailing growth habit. The new cultivar was selected as a single flowering plant within the progeny of the above stated cross-pollination during September 2018 in a controlled environment in Arroyo Grande, California.

Asexual reproduction of the new cultivar by terminal stem cuttings since September 2018 in Arroyo Grande, California and West Chicago, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balmecoplum' as a new and distinct cultivar of *Sutera* plant:

1. Dark purple-colored flowers;
2. Dark green-colored foliage;
3. Low growth vigor; and
4. Mounded-trailing growth habit.

Plants of the new cultivar differ from plants of the female and male parents primarily in having dark purple-colored flowers that are different from the medium pink-colored flowers of the female parent and from the medium violet-blue colored flowers of the male parent.

Of the many commercially available *Sutera* cultivars, the most similar in comparison to the new cultivar is MegaCopa Pink Shine 'Balmecopine', not patented. However, in side-by-side comparison, plants of the new cultivar differ from plants of 'Balmecopine' in at least the following characteristic: Plants of the new cultivar have a darker flower color than plants of 'Balmecopine'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balmecoplum'. The plants were approximately 16-weeks old. The plants were grown in 4.5-inch containers for approximately 11 weeks in a greenhouse in West Chicago, Illinois. Plants were given one pinch at transplant.

DETAILED BOTANICAL DESCRIPTION

Figure 1:
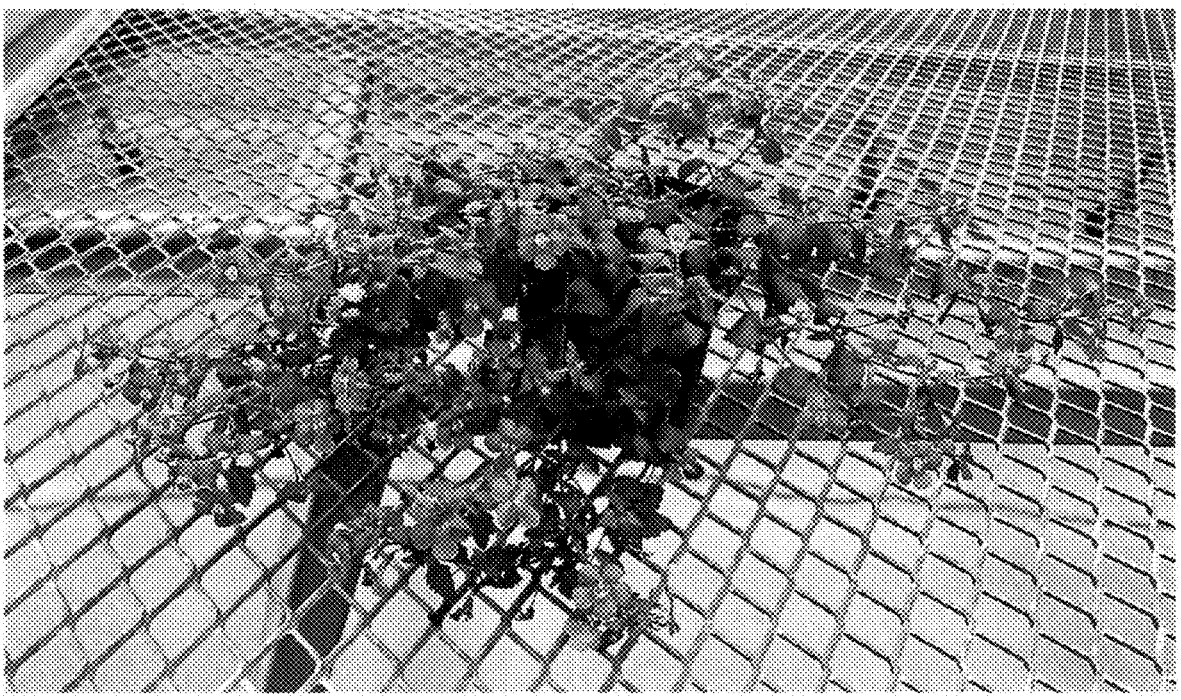
FIG. 1 illustrates a side view of the overall growth and flowering habit of 'Balmecoplum'.
Figure 2:
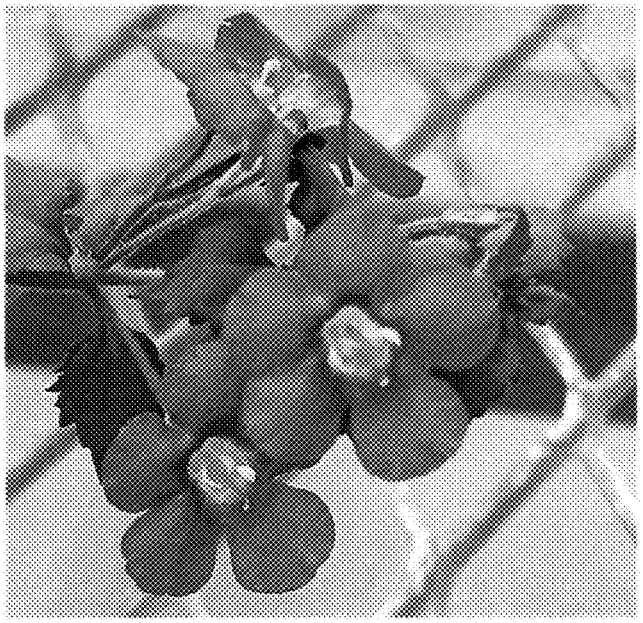
FIG. 2 illustrates a close-up view of an individual flower of 'Balmecoplum'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in February 2023 under natural light conditions in Naperville, Illinois.

The following descriptions and measurements describe approximately 16-week-old plants produced from cuttings from stock plants and grown in a polycarbonate greenhouse under conditions comparable to those used in commercial practice. The plants were grown in West Chicago, Illinois in 4.5-inch containers for approximately 11 weeks utilizing a soilless growth medium. Plants were one pinch at transplant. Greenhouse temperatures were maintained at approximately 68° F. to 70° F. (20° C. to 21° C.) during the day and approximately 60° F. to 65° F. (16° C. to 18° C.) during the night. Supplemental lighting was used. Measurements and numerical values represent averages of typical plants.

Botanical classification: *Sutera cordata* 'Balmecoplum'.

Parentage:

*Female parent.*—Proprietary *Sutera cordata* breeding selection coded SUT-1039-004, not patented.

*Male parent.*—Proprietary *Sutera cordata* breeding selection coded SUT-0906-001, not patented.

Propagation:

*Type cutting.*—Terminal stem.

*Time to initiate roots.*—Approximately 6 to 8 days.

*Time to produce a rooted cutting.*—Approximately 3 weeks.

*Root description.*—Fibrous.

*Rooting habit.*—Freely branching.

Plant description:

*Commercial crop time.*—Approximately 5 to 7 weeks from a rooted cutting to finish in a 10 cm container.

*Growth habit and general appearance.*—Low growth vigor, mounded-trailing growth habit.

*Size.*—Height from soil level to top of plant plane: Approximately 7.5 cm. Width: Approximately 44.0 cm.

*Branching habit.*—Freely branching, pinching increases basal branching. Quantity of main branches per plant: Approximately 8.

*Branch.*—Strength: Strong, slightly flexible. Length: Approximately 22.0 cm. Diameter: Approximately 2.0 mm. Length of central internode: Approximately 2.5 cm. Texture: Densely pubescent with a mixture of glandular and non-glandular hairs. Gland color: Colorless, transparent. Color of young stems: 144A. Color of mature stems: 146B.

Foliage description:

*General description.*—Quantity of leaves per main branch: Approximately 18. Fragrance: None detected. Form: Simple. Arrangement: Opposite.

*Leaves.*—Aspect: Acute angle to perpendicular to stem. Shape: Ovate. Margin: Serrate, ciliate. Apex: Broadly acute. Base: Rounded. Venation pattern: Pinnate. Length of mature leaf: Approximately 2.0 cm. Width of mature leaf: Approximately 2.1 cm. Texture of upper surface: Sparsely pubescent. Texture of lower surface: Sparsely pubescent on venation only. Color of upper surface of young and mature foliage: 137A with indistinguishable venation. Color of lower surface of young and mature foliage: Closest to 138A with venation of 146D to indistinguishable.

*Petiole.*—Length: Approximately 6.0 mm. Width: Approximately 1.5 mm. Texture: Moderately pubescent. Color: 146D.

Flowering description:

*Flowering habit.*—'Balmecoplum' is freely flowering under outdoor growing conditions with substantially continuous blooming from early spring through autumn and year-round in greenhouse environment.

*Lastingness of individual flower on the plant.*—Approximately 6 to 9 days.

Flower description:

*General description.*—Type: Simple, salverform. Quantity per plant: Approximately 50. Fragrance: None detected.

*Bud.*—Rate of opening: Generally takes 2 to 3 days for bud to progress from first color to fully open flower. Quantity per plant: Approximately 19.

*Bud just before opening.*—Shape: Obovoid. Length: Approximately 7.0 mm. Diameter: Approximately 3.0 mm. Texture: Glabrous. Color: 84D.

*Corolla.*—Diameter: Approximately 2.1 cm.

*Petals.*—Quantity: 5, fused to form a tube. Shape: Obovate. Appearance: Matte. Margin: Entire, slightly wavy. Apex: Rounded. Length from tube: Approximately 8.0 mm. Width: Approximately 9.0 mm. Texture of upper surface: Glabrous, with sparsely pubescent base. Texture of lower surface: Glabrous. Color of upper surface when first open: N82A with an overlay of N81A at base. Color of lower surface when first and fully open: N82C to N82D. Color of upper surface when fully open: N82A to N82B.

*Corolla tube.*—Length: Approximately 1.0 cm. Diameter at distal end: Approximately 4.0 mm. Diameter at proximal end: Approximately 1.0 mm. Texture of inner surface: Densely pubescent at throat opening. Texture of outer surface: Densely glandular pubescent. Gland color: Colorless, transparent. Color of inner surface: NN155D with N25A and 21A at throat opening. Color of outer surface: NN155D with an underlay of N25A.

*Calyx.*—Shape: Cupped. Length: Approximately 7.0 mm. Width: Approximately 4.0 mm.

*Sepals.*—Quantity per flower: 5, fused at base. Shape: Linear. Margin: Entire. Apex: Acute. Length: Approximately 7.0 mm. Width: Approximately 1.0 mm. Texture of upper (inner) surface: Densely glandular pubescent. Texture of lower (outer) surface: Moderately pubescent. Gland color: Colorless, transparent. Color of upper and lower surfaces: 137A.

*Peduncle.*—Strength: Strong, flexible. Aspect: Acute angle to stem. Length: Approximately 1.0 cm. Diameter: Approximately 1.0 mm. Texture: Densely pubescent with a mixture of glandular and non-glandular hairs. Gland color: Colorless, transparent. Color: 146B.

*Reproductive organs.*—Androecium: Stamen quantity: 4, didynamous, base adnate to corolla tube. Stamen length of longer pair: Approximately 1.0 cm. Stamen length of shorter pair: Approximately 8.0 mm. Filament length of fixed portion: Approximately 6.0 mm. Filament color: NN155D. Anther shape: Obovate.

Anther length: Approximately 1.0 mm. Anther color: 13C and NN155D at base. Pollen amount: Abundant. Pollen color: 13B. Gynoecium: Pistil quantity: 1 per flower. Pistil length: Approximately 1.2 cm. Stigma shape: Linear slightly arched, rounded apex. Stigma length: Approximately 1.0 mm. Stigma color: 145B. Style length: Approximately 1.0 cm. Style color: 145D. Ovary diameter: Approximately 1.0 mm. Ovary color: 144A.

Seed and fruit production: Neither seed nor fruit production has been observed.

Disease and pest resistance: Resistance to pathogens and pests common to *Sutera* has not been observed.

What is claimed is:

1. A new and distinct cultivar of *Sutera* plant named 'Balmecoplum' substantially as herein illustrated and described.

* * * * *